US00PP30113P2

(12) United States Plant Patent
Ammerlaan

(10) Patent No.: US PP30,113 P2
(45) Date of Patent: Jan. 15, 2019

(54) ***GASTERALOE* PLANT NAMED 'OVROCKS05'**

(50) Latin Name: ***Gasteraloe* hybrid Guillaumin.**
Varietal Denomination: OVROCKS05

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/732,866

(22) Filed: Jan. 5, 2018

(30) Foreign Application Priority Data

Oct. 12, 2017 (QZ) ..... PBR 2017/2561

(51) Int. Cl.
*A01H 5/00* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Kent L Bell
(74) *Attorney, Agent, or Firm* — Samuel R. McCoy, Jr.

(57) ABSTRACT

A new and distinct variety of *Gasteraloe* plant named 'OVROCKS05' which is characterized by a broad ovate plant form, upright narrowly deltoid foliage that is spirally arranged in a basal rosette, a rosette which is centered with a light green general coloration that becomes progressively darker towards the outer whorls of foliage, as well as the stability of these characteristics from generation to generation.

4 Drawing Sheets

Latin name of the genus and species: The Latin name of the genus and species of the novel variety disclosed herein is *Gasteraloe* hybrid Guillaumin.

Variety denomination: The inventive variety of *Gasteraloe* disclosed herein has been given the variety denomination 'OVROCKS05'.

CROSS REFERENCE TO RELATED APPLICATIONS

This application claims priority to the Community Plant Variety Rights application number 2017/2561, filed on Oct. 12, 2017, which is herein incorporated by reference.

BACKGROUND OF THE INVENTION

Parentage: 'OVROCKS05' originated as a naturally occurring, whole-plant mutation of an unnamed *Gasteraloe* hybrid plant (not patented). In March of 2013 the inventor discovered the mutation at a commercial greenhouse in Bleiswijk, the Netherlands, growing amongst a crop of the unnamed plant. The mutation was noted for its unique foliage and growth habit and was subsequently isolated for further evaluation in order to confirm the distinctness and stability of the characteristics first observed. Upon confirmation of distinctness and stability, 'OVROCKS05' was selected for commercialization.

Asexual Reproduction: Asexual reproduction of the new cultivar 'OVROCKS05', by way of rooting leaf cuttings, was first initiated in March of 2013 at the inventor's commercial greenhouse in Bleiswijk, the Netherlands. The claimed plant has since been asexually propagated by way of meristematic tissue culture propagation. Through five subsequent generations, the unique features of this cultivar have proven to be stable and true to type.

SUMMARY OF THE INVENTION

The cultivar 'OVROCKS05' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS05'. These characteristics in combination distinguish 'OVROCKS05' as a new and distinct *Gasteraloe* cultivar:

1. 'OVROCKS05' exhibits a broad ovate plant form with foliage that is spirally arranged in a basal rosette; and
2. 'OVROCKS05' exhibits a rosette of foliage which is centered with a light green general coloration which becomes progressively darker towards the outer whorls of foliage; and
3. 'OVROCKS05' exhibits long, narrowly deltoid foliage which is held upright; and
4. 'OVROCKS05' exhibits juvenile foliage towards the center of the rosette which is light green at the base and progressively darker green towards the apex, and densely covered with green-white protuberances; and
5. 'OVROCKS05' exhibits dark green mature foliage towards the outer whorls of the rosette which is densely covered with light green protuberances.

BOTANICAL DESCRIPTION OF THE PLANT

Figure 1:
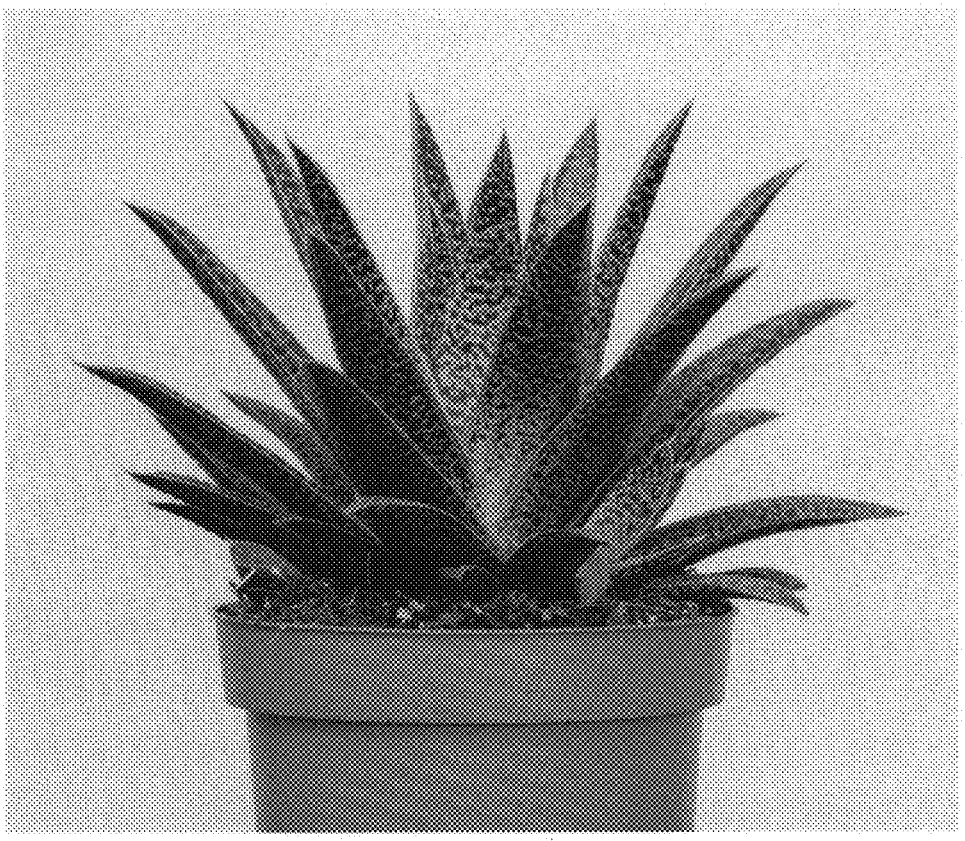
FIG. 1 illustrates, as nearly true as it is reasonably possible to make the same in color photographs of this type, an exemplary plant of 'OVROCKS05' grown in a commercial greenhouse in Bleiswijk, the Netherlands. This plant is approximately 14 months old, shown planted in a 10.5 cm container.
Figure 2:
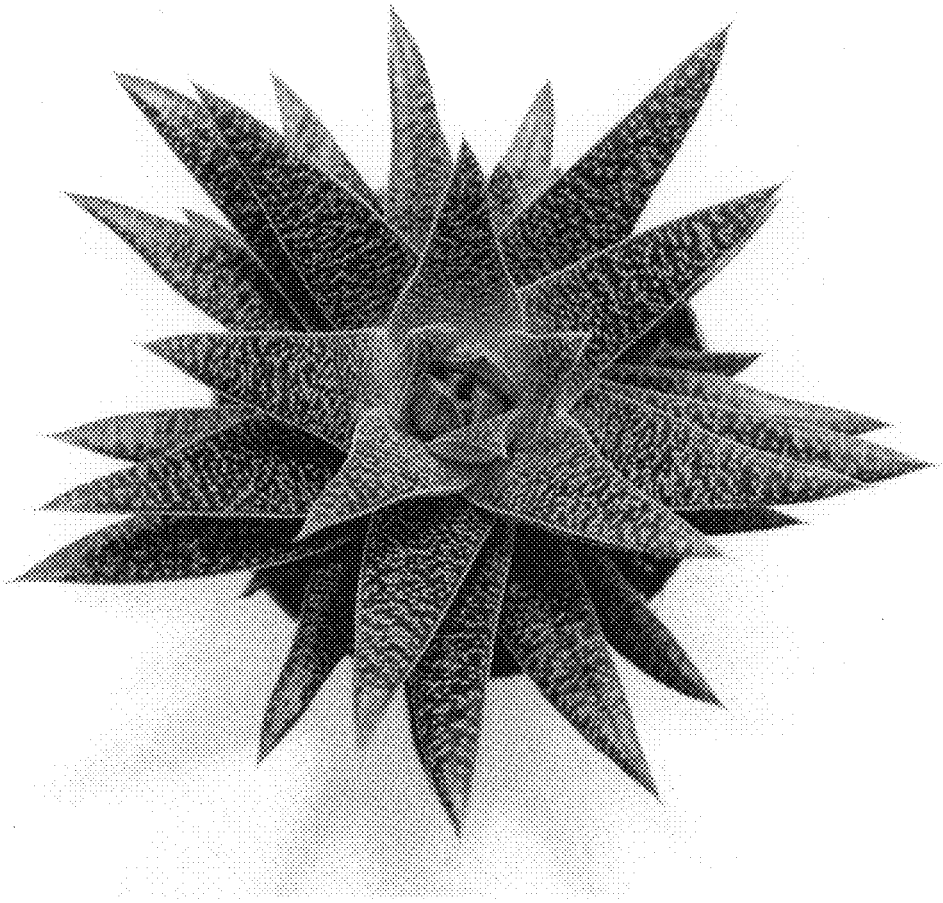
FIG. 2 illustrates, as nearly true as it is reasonably possible to make the same in color photographs of this type, the typical foliage arrangement of 'OVROCKS05'.
Figure 3:
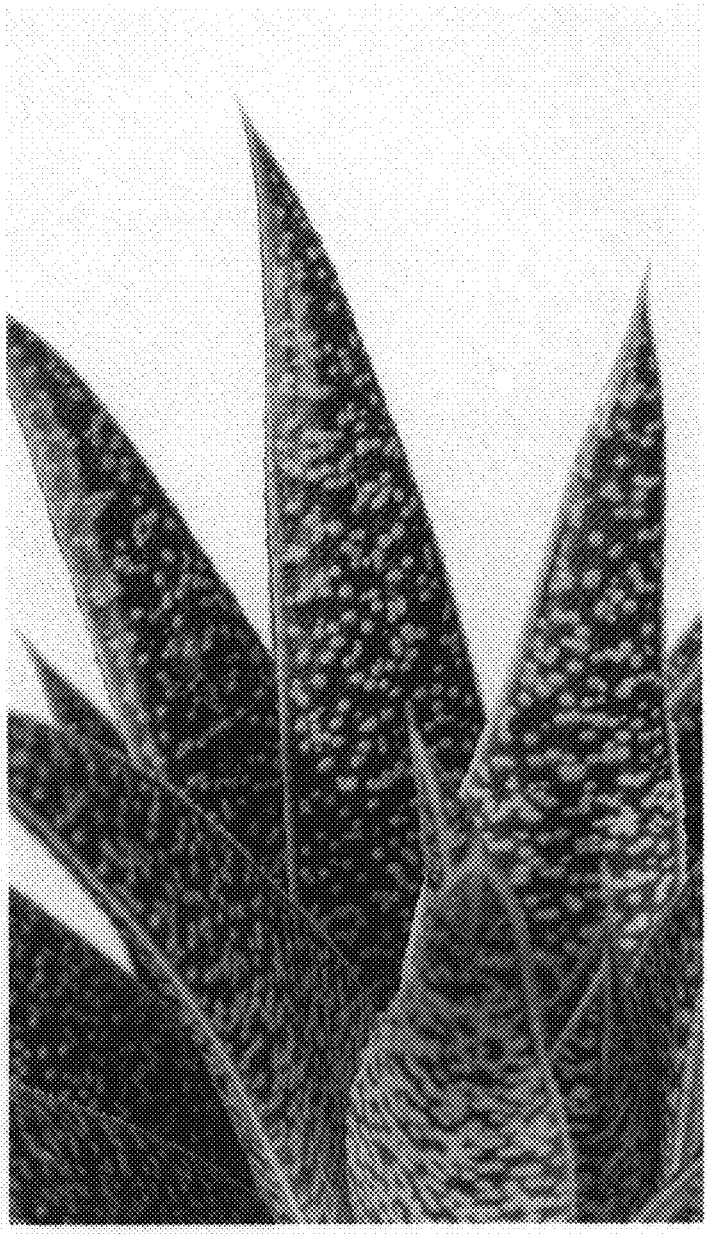
FIG. 3 illustrates, as nearly true as it is reasonably possible to make the same in color photographs of this type, the adaxial surface of the mature foliage 'OVROCKS05'.
Figure 4:
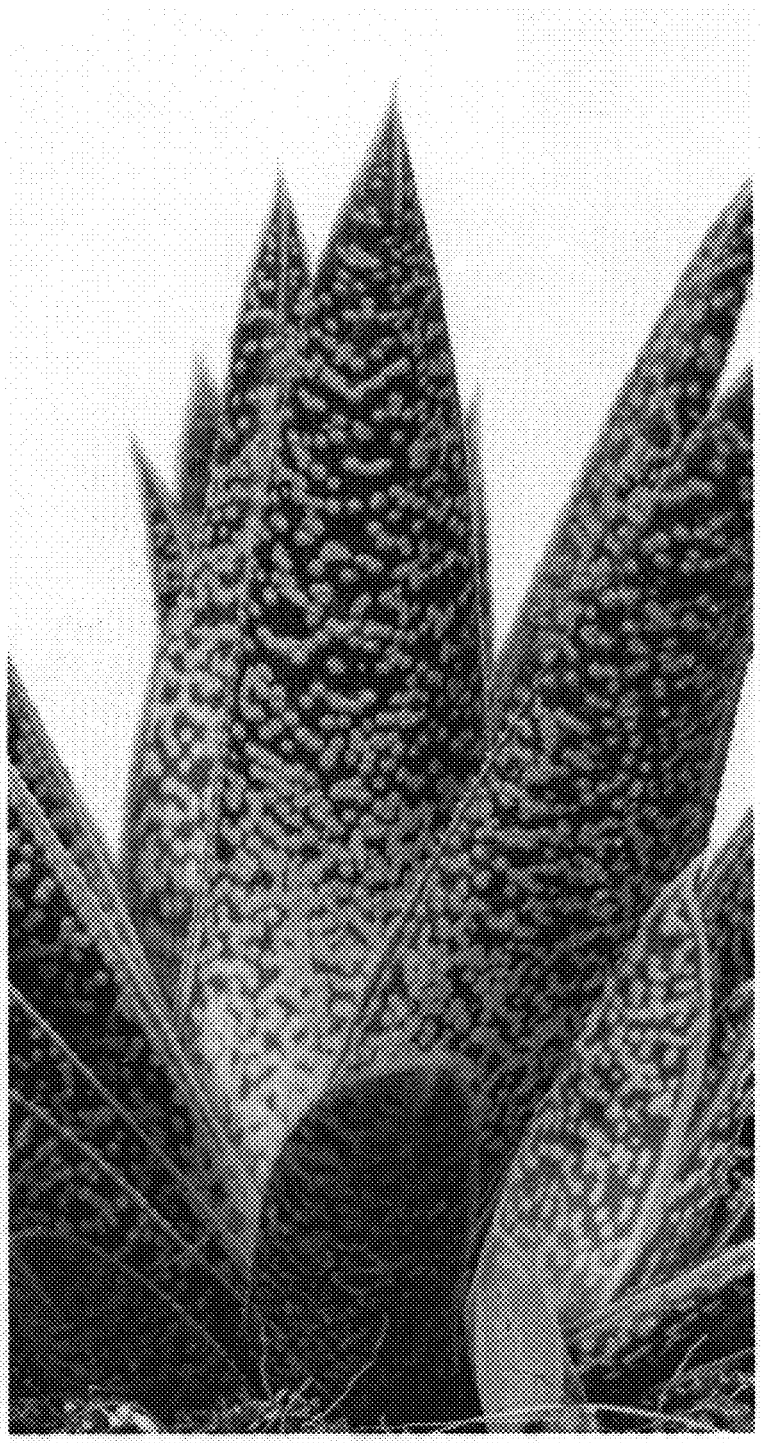
FIG. 4 illustrates, as nearly true as it is reasonably possible to make the same in color photographs of this type, the abaxial surface of the mature foliage 'OVROCKS05'.

The following observations and measurements made in June of 2017 describe averages from a sample set of six specimens of 14 months old 'OVROCKS05' plants grown in 10.5 cm nursery containers at a commercial greenhouse in Bleiswijk, the Netherlands. Plants were produced using conventional greenhouse production protocols for *Gasteraloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS05' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS05' and a comparison with the unnamed plant and closest known comparator is provided below.

Plant description:

*Growth habit*.—Succulent perennial with foliage growing in a non-branched basal rosette.

*Plant form*.—Broad ovate.

*Height from soil level to top of foliar plane*.—13.1 cm.

*Plant spread*.—Average of 19.0 cm.

*Growth rate*.—Moderate.

*Plant vigor*.—Moderate.

*Propagation*.—Type — Leaf cuttings. Time to initiate rooting — Approximately 4 months at 21 degrees Celsius. Crop time — Approximately 14 months to produce a marketable plant in a 10.5 cm container.

*Disease and pest resistance or susceptibility*.—Neither resistance nor susceptibility to typical *Gasteraloe* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Spirally placed in a rosette.

*Division*.—Simple.

*Attachment*.—Sessile.

*Quantity*.—Approximately 38 leaves per rosette.

*Shape*.—Narrow deltoid succulent leaves.

*Dimensions*.—10.4 cm long, 3.0 cm wide, and 0.8 cm thick, on average.

*Aspect*.—Flat.

*Attitude*.—At an average angle of 40 degrees to the soil level.

*Apex*.—Narrow apiculate with a soft mucronate tip.

*Base*.—Broad cuneate.

*Margin*.—Finely dentate; teeth have an average length of 0.05 cm and are colored green, nearest to RHS 138C but lighter. Margins are not undulated or lobed.

*Texture, adaxial surface*.—Glabrous and densely covered with protuberances, presenting as orbicular dots, each approximately 0.5 mm high and 1.2 mm in diameter.

*Texture, abaxial surface*.—Glabrous and densely covered with protuberances, presenting as orbicular, each approximately 0.5 mm high and 1.2 mm in diameter; papilla bearing short, soft spines towards the apex.

*Luster, adaxial surface*.—Moderately glossy.

*Luster, abaxial surface*.—Moderately glossy.

*Color*.—Juvenile foliage, adaxial surface — Yellow-green, nearest to RHS 144A; nearest to in between green and yellow-green towards the apex, RHS NN137A and 147A; fading to greyed-green towards the base, nearest to in between RHS 193B and 193C; leaf densely covered with protuberances which are colored green-white, nearest to RHS 157D. Juvenile foliage, abaxial surface — Green, nearest to a mixture of RHS 143B and 143C; darker towards the apex, nearest to RHS N137A; fading to greyed-green towards the base, nearest to a mixture of RHS 193B and 193C; leaf densely covered with protuberances which are colored green-white, nearest to RHS 157D. Mature foliage, adaxial surface — Nearest to in between green, RHS 139A, and greyed-green, RHS N189A, but darker; leaf densely covered with protuberances which are colored green-white, nearest to RHS 157D. Mature foliage, abaxial surface — Greyed-green, nearest to RHS N189A; leaf densely covered with protuberances which are colored green, nearest to RHS 138B. Venation — No venation is visible.

*Petiole*.—No petiole; leaves are sessile.

Inflorescence: No flowering has been observed to date.

COMPARISONS WITH THE PARENT PLANT

Plants of the new cultivar 'OVROCKS05' differ from the parent, an unnamed *Gasteraloe* plant hybrid (not patented), in the following characteristics described in Table 1 below.

TABLE 1

Comparison with the unnamed Gasteraloe plant

| Characteristic | 'OVROCKS05' | The unnamed Gasteraloe plant |
|---|---|---|
| Foliage thickness. | Thinner than the parent. | Thicker than 'OVROCKS05'. |
| Foliage width. | Narrower than the unnamed Gasteraloe plant | Wider than 'OVROCKS05'. |

TABLE 1-continued

| Comparison with the unnamed Gasteraloe plant | | |
|---|---|---|
| Characteristic | 'OVROCKS05' | The unnamed Gasteraloe plant |
| Foliage margins. | Finely dentate with more spine-like teeth than the unnamed Gasteraloe plant | Finely dentate with fewer spine-like teeth than 'OVROCKS05'. |
| General coloration of the juvenile foliage. | Lighter green. | Darker green. |

COMPARISONS WITH THE CLOSEST KNOWN COMPARATOR

Plants of the new cultivar 'OVROCKS05' differ from the commercial variety, *Gasteraloe* 'WT03' (Community Plant Variety Rights grant number 30451) in the following characteristics described in Table 2 below.

TABLE 2

| Comparison with a comparison plant | | |
|---|---|---|
| Characteristic | 'OVROCKS05' | 'WT03' |
| Foliage attitude. | More upright. | Less upright. |
| Foliage width. | Narrower than 'WT03'. | Wider than 'OVROCKS05'. |
| General coloration of the juvenile foliage. | Lighter green. | Darker green. |
| General coloration of entire rosette. | Light green inner whorls of foliage, and progressively darker green towards the outer whorls. | Inner and outer whorls are a consistent dark green. |

That which is claimed is:

1. A new and distinct variety of *Gasteraloe* plant named 'OVROCKS05', substantially as described and illustrated herein.

* * * * *